(12) United States Patent
Chen et al.

(10) Patent No.: US 9,206,120 B2
(45) Date of Patent: Dec. 8, 2015

(54) CLEAN METHOD FOR PREPARING D,L-METHIONINE

(71) Applicants: ZHEJIANG NHU COMPANY LTD., Shaoxing, Zhejiang Province (CN); ZHEJIANG UNIVERSITY, Hangzhou, Zhejiang Province (CN); SHANDONG NHU AMINO ACIDS CO., LTD., Weifang, Shandong Province (CN)

(72) Inventors: Zhirong Chen, Hangzhou (CN); Cunchao Wang, Shaoxing (CN); Chuqiu Zhao, Shaoxing (CN); Sujuan Wang, Shaoxing (CN); Chengfeng Zhang, Shaoxing (CN); Tao Long, Shaoxing (CN); Xinhong Liu, Shaoxing (CN)

(73) Assignees: ZHEJIANG NHU COMPANY LTD., Shaoxing (CN); ZHEJIANG UNIVERSITY, Hangzhou (CN); SHANDONG NHU AMINO ACIDS CO., LTD., Weifang (CN)

( * ) Notice: Subject to any disclaimer, the term of this patent is extended or adjusted under 35 U.S.C. 154(b) by 0 days.

(21) Appl. No.: 14/425,310

(22) PCT Filed: Jan. 6, 2013

(86) PCT No.: PCT/CN2013/070129
§ 371 (c)(1),
(2) Date: Mar. 2, 2015

(87) PCT Pub. No.: WO2014/032401
PCT Pub. Date: Mar. 6, 2014

(65) Prior Publication Data
US 2015/0284323 A1    Oct. 8, 2015

(30) Foreign Application Priority Data

Sep. 3, 2012   (CN) .......................... 2012 1 0320297

(51) Int. Cl.
| | |
|---|---|
| *C07C 323/00* | (2006.01) |
| *C07C 321/00* | (2006.01) |
| *C07C 45/00* | (2006.01) |
| *C07C 319/20* | (2006.01) |
| *C07D 207/38* | (2006.01) |

(52) U.S. Cl.
CPC ............ *C07C 319/20* (2013.01); *C07D 207/38* (2013.01)

(58) Field of Classification Search
CPC ............................ C07C 319/20; C07C 323/00
USPC ...................................... 562/556, 559; 568/41
See application file for complete search history.

(56) References Cited

U.S. PATENT DOCUMENTS

| | | | | |
|---|---|---|---|---|
| 5,990,349 A | * | 11/1999 | Geiger et al. .................. | 562/559 |
| 8,735,631 B2 | * | 5/2014 | Devaux et al. .................. | 568/41 |
| 2008/0242888 A1 | * | 10/2008 | Fujita et al. .................... | 562/559 |
| 2010/0121104 A1 | * | 5/2010 | Azemi et al. .................... | 562/559 |
| 2011/0319659 A1 | * | 12/2011 | Yoshikawa et al. ............ | 562/559 |

FOREIGN PATENT DOCUMENTS

| | | |
|---|---|---|
| CN | 1589259 A | 3/2005 |
| CN | 101602700 A | 12/2009 |
| CN | 102796033 A | 11/2012 |

* cited by examiner

*Primary Examiner* — Sikarl Witherspoon
(74) *Attorney, Agent, or Firm* — Jiwen Chen

(57) ABSTRACT

The present invention discloses a clean method for preparing a D,L-methionine comprising the steps of: preparing a potassium cyanide solution using a crystallized mother solution containing potassium carbonate as an absorbing liquid to absorb hydrocyanic acid, then reacting the potassium cyanide solution with 3-methylthio propionaldehyde and an ammonium bicarbonate solution at 50-150° C. for 3-15 minutes so as to obtain a 5-(β-methylthioethyl)glycolyurea solution, then bring the 5-(β-methylthioethyl)glycolyurea solution to a temperature of 140-220° C. and subjecting to a saponification reaction for 2-5 minutes, after the completion of the saponification, reducing the temperature to 0-40° C., extracting with an organic solvent, neutralizing the water phase with $CO_2$ and crystallizing, then filtering, washing, and drying to obtain an acceptable D,L-methionine product; bring the crystallized D,L-methionine mother solution from filtration to a temperature to 110-160° C. to remove $CO_2$, which are all then circulated and used as a hydrocyanic acid-absorbing liquid. The process route of the present invention is a route suitable for a continuous and clean production, substantially without producing waste water and waste gas.

9 Claims, 1 Drawing Sheet

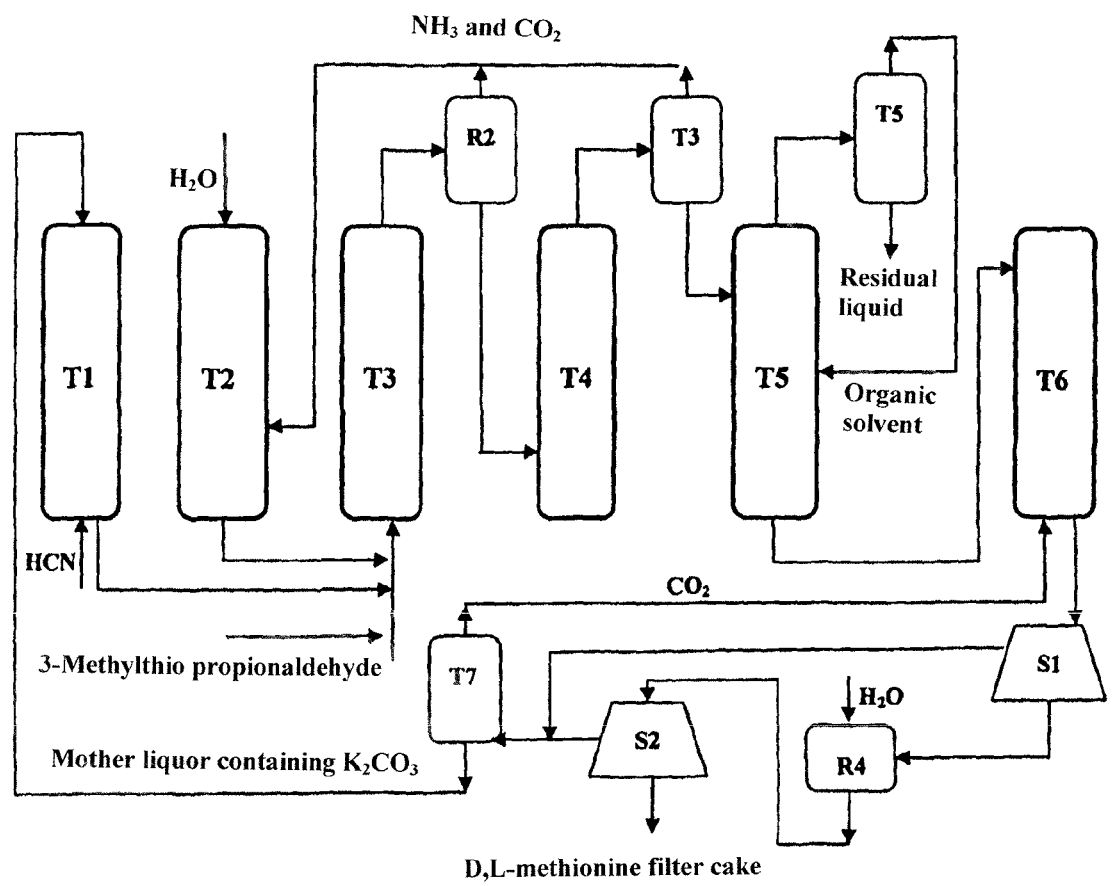

CLEAN METHOD FOR PREPARING D,L-METHIONINE

This is a U.S. national stage application of PCT Application No. PCT/CN2013/070129 under 35 U.S.C. 371, filed Jan. 6, 2013 in Chinese, claiming the priority benefit of Chinese Application No. 201210320297.0, filed Sep. 3, 2012, which is hereby incorporated by reference.

TECHNICAL FIELD

The present invention is related to the compound synthesis field, more specifically, a clean method for preparing D,L-methionine.

BACKGROUND OF THE INVENTION

D,L-methionine is a sulfur-containing amino acid essential to human body and is closely related to metabolism of various sulfur-containing compounds in biological organisms. Methionine belongs to the first restrictive amino acid and cannot be synthesized inside animal body and needs to be taken from the food. Adding methionine into the feedstuffs can promote growth of livestocks, increase lean meat percentage, and shorten the feeding cycle. Methionine can also be used for prevention and treatment of liver diseases such as chronic or acute hepatitis and hepatic cirrhosis because methyl group contained in methionine can be used for methylation of toxicants or medicines and thus have detoxification effect. Methionine can also be used for alleviation of toxic reaction of hazardous substances such as arsenic, trichloride, carbon tetrachloride, benzene, pyridine and quinoline. According to relevant statistical information, market demand for methionine worldwide has reached 1,000,000 ton/year. The demand for methionine in international market is increasing at a year-to-year growth rate of 4% in recent years; whereas the demand in China is increasing at a year-to-year growth rate of 7%.

As introduced in relevant literatures, there are following methods for synthesis of D,L-methionine:

In the patent publication with the publication number of CN1923807A, Sumitomo Chemical Co., Ltd. from Japan proposes to prepare D,L-methionine through hydrolysis of 5-(β-methylthioethyl)glycolyurea with Alkaline potassium compounds, then acidification with pressurized $CO_2$ gas, and then fractionized condensation and crystallization with addition of polyvinyl alcohol. Although such method can recycle $CO_2$ gas, due to factitious addition of polyvinyl alcohol, the crystallization mother solution as discharged cannot be recycled and can only be wasted, which produces a large quantity of wastewater S and N containing organic compounds. Furthermore, fractionized condensation method consumes a large quantity of thermal energy to the extent of resulting in significant increase in product cost for D,L-methionine.

In the patent publication with the publication number of CN85108505A, Wang Jianhua proposes to add a mixture of neutral amino acid and organic acid, containing 10% acrolein, as the catalyst during preparation of 5-(β-methylthioethyl) glycolyurea; it aims to prepare 5-(β-methylthioethyl)glycolyurea with a one-step method by using methanethiol and acrolein, simplify operation process, and improve preparation yield of 5-(β-methylthioethyl)glycolyurea. However, a mixture of neutral amino acid and organic acid that is intentionally added for further saponification with the addition of alkaline substances inevitably participates in the reaction, and produces metal salt. As a result, the metal salts accumulated in the mother solution so that the mother solution cannot be recycled and produces a large quantity of wastewater S and N containing organic compounds.

In the patent publication with the publication number of CN85108531A, Wang Jianhua proposes to produce D,L-methionine through saponification of 5-(β-methylthioethyl)glycolyurea with alkaline sodium compounds, acidification with vitriol and separation with fractionized condensation and crystallization method. Such method may produce a large quantity of by-products such as sodium sulfate, separation and processing of sodium sulfate will become a significant burden for production.

In the patent publication with the publication number of CN1589259A, to obtain a methionine preparation method that can stably produce a granular or tabular methionine crystal of high bulk density and quality, Nippon Soda Co., Ltd. proposes to use one intermetallic compound selected from metal hydroxide, metal carbonate or metal carbonate salt to hydrolyze 5-(β-methylthioethyl)glycolyurea to obtain the methionine metal salt, then neutralize the methionine metal salt by using pressurized $CO_2$ gas to realize crystallization of methionine. After that, the methionine is separated from the filtrate, and one makes sure that the filtrate can be recycled for hydrolysis of 5-(β-methylthioethyl)glycolyurea during preparation of methionine. According to this method, despite of the fact that partial mother solution for crystallization is again used for hydrolysis, some tailings and by-products are not eliminated during intermediate process and are inevitably accumulated to the extent of affecting application effect and product quality. Meanwhile, because the mother solution is not used for preparation of 5-(β-methylthioethyl)glycolyurea, a large quantity of water is required, causing the water amount cannot be balanced over the whole process. Furthermore, each use will consume a large quantity of water as required by preparation of 5-(β-methylthioethyl)glycolyurea.

In the patent publication with the publication number of CN1103066A, Degussa AG proposes a synthesis technique to obtain an amino nitrile compound through reaction among methylthio propionaldehyde, HCN and ammonia, and hydrolyze amino nitrile compound with a ketone catalyst to obtain the aminoamide, and then finally prepare methionine through high-temperature hydrolysis with an alkaline catalyst. Such methionine synthesis method also has some defects despite of the fact that it is provided with unique features as compared with industrialized production method, The most serious defect lies in a large quantity of wastewater as produced; for instance, aminoamide obtained through addition of ketone catalyst during its preparation shall subject to separation and purification by passing through column, such separation and purification method is inappropriate for such bulk product during industrialized production. Viewed from overall techniques, it fails to solve the problem of a large quantity of waste water.

In the patent publication with the publication number of CN102399177A, Li Kuanyi proposes a green and clean technical method for continuous synthesis of methionine: taking methylthio propionaldehyde as synthesized with acrolein and methanthiol as the material for reaction with hydrogen cyanide to obtain the intermediate 2-hydroxy-4-(methylthio)nitrile; further obtaining hydantoin solution through continuous reaction of the intermediate 2-hydroxy-4-(methylthio)nitrile in the first reaction bed of combined reactor in the presence of excessive ammonia and carbon dioxide. The hydantoin solution will flow out of the first reaction bed, and release excessive carbon dioxide and ammonia in the desorption column. The hydantoin solution subjecting to desorption will flow in the second reaction bed of the combined reactor for hydrolysis under alkaline conditions to obtain the methionine potassium solution. The methionine potassium solution with carbon dioxide are neutralized to obtain methionine and potassium hydrogen carbonate solution. Methionine is separated from the solution by means of crystallization; whereas potassium hydrogen carbonate and mother solution shall be subject to further treatment for recycling. It appears that this technical approach is extremely clean and appropriate for industrialized production. However, according to its patent introduction and analysis from the angle of industrialized production, it still has some disadvantages. First, such technique requires a large quantity of water for reaction during preparation of hydantoin solution; whereas mother solution for crystallization is used for hydrolysis other than preparation of hydantoin. As a result, a large quantity of water is distilled for preparation of hydantoin during hydrolysis to further apply remaining mother solution for hydrolysis of hydantoin. This process results in increased production cost because it requires a large amount of thermal and electric energies. Second, delayed elimination of by-products as produced during chemical reaction in the whole technological process may seriously affect the quality of final products, and making it more difficult for purification of final products. Meanwhile, it also affects the consumption and batch of mother solution. This results in increased emission of wastewater during industrialized production.

As proposed in US2004/0039228A1, D,L-methionine can be obtained through reaction among some mother solution for crystallization, certain amount of $NH_3$ and $CO_2$ at the temperature of 60° C. in the presence of $TiO_2$, the catalyst, saponification at the temperature of 180-300° C. and neutralization with $CO_2$. Despite of the fact that such method makes use of partial crystallization mother solution indiscriminately to minimize the emission of wastewater, it will result in the following problems due to addition of as $TiO_2$ catalyst in the technological process: if all mother solution for crystallization is used indiscriminately, it will result in accumulation of $TiO_2$; Furthermore, D,L-methionine subjecting to crystallization and filtration will also contain $TiO_2$ and thus the product will contain metal Ti that will result in reduced product quality, which makes follow-up treatment more complicated and difficult.

In the patent publication with the publication number of EB1761074A1(CN101602700A), Sumitomo Chemical puts forward the following method: using alkaline potassium compound as the catalyst for saponification of 5-(β-methylthioethyl)glycolyurea; using $CO_2$ for neutralization and crystallization; using crystallization mother solution subjecting to aforesaid fractionized concentration and crystallization for saponification of reaction fluid of follow-up 5-(β-methylthioethyl)glycolyurea indiscriminately; adding polyvinyl alcohol into the remaining mother liquor subjecting to secondary concentration for crystallization. At this point, mother solution is abandoned other than indiscriminate use. Such technique is used by Sumitomo Chemical for industrialized production of D,L-methionine. However, there are numerous problems with this technique, especially on the aspect of green and clean production. Only partial crystallization mother solution is used. Most of crystallization mother solution is abandoned after one-time use, which produces a large quantity of wastewater.

SUMMARY OF THE INVENTION

In view of excessive amount of wastewater with N and S containing organic compounds—produced during industrialized production of D,L-methionine and serious environmental pollution, a major technical problem solved by the present invention is to provide a DL-methionine preparation method that is clean and easy to operate.

For this purpose, the present invention provides a clean method for preparing D,L-methionine, comprising the following steps:

(1) preparing 5-(β-methylthioethyl)glycolyurea reaction fluid by using 3-methylthio propionaldehyde, KCN and $NH_4HCO_3$ solution as raw materials for continuous reaction in a tubular reactor that is gradually heated;

(2) proceeding with decompression of aforesaid 5-(β-methylthioethyl)glycolyurea reaction fluid to separate $NH_3$ and $CO_2$ from the reaction fluid for delivery to another tubular reactor for decomposition and saponification to obtain a saponification fluid;

(3) eliminating the produced $NH_3$ and $CO_2$ during saponification through desorption of the saponification fluid to obtain D, L-methionine potassium solution;

(4) obtaining $NH_4HCO_3$ solution through spraying with water to the absorbed $NH_3$ and $CO_2$ as separated in Steps (2) and (3), and directly using the $NH_4HCO_3$ solution as the raw material for preparation of 5-(β-methylthioethyl)glycolyurea reaction fluid in Step (1);

(5) cooling down D,L-methionine potassium solution obtained in Step (3), and then using an organic solvent for reversed and continuous extraction; directly using the organic solvent recycled through distillation of an organic solvent layer for reversed and continuous extraction; raffinate produced by distillation is treated as a waste fluid;

(6) delivering water as produced through reversed and continuous extraction in Step (5) to the continuous crystallizer, simultaneously delivering $CO_2$ gas to the continuous crystallizer for acidification to control PH value of reaction fluid in the continuous crystallizer at 6-9, and then obtaining crystallization intermixture;

(7) separating solid and liquid in the crystallization intermixture to obtain the crude D,L-methionine product and crystallization mother solution; washing crude D,L-methionine product with water for solid-liquid separation to obtain filter cake of D,L-methionine and washing filtrate;

(8) drying the filter cake of D,L-methionine under the protection of an inert gas to obtain D,L-methionine product;

(9) combining the crystallization mother solution in Step (7) with washing filtrate for delivery to the decomposition column to fully decompose $KHCO_3$ into $K_2CO_3$ for release of $CO_2$ gas; released $CO_2$ gas subjecting to compression is delivered to a continuous crystallizer for acidification and crystallization;

(10) using $K_2CO_3$-containing mother solution obtained in Step (9) for absorption of HCN gas to prepare a KCN solution that is used as the material for preparation of 5-(β-methylthioethyl)glycolyurea in Step (1).

In the Step (1), the preferred mole ratio of 3-methylthio propionaldehyde, KCN and $NH_4HCO_3$ is 1:1-1.1:2-3. At this point, an optimal single-pass conversion rate of 3-methylthio propionaldehyde and equipment utilization rate can be obtained.

In the Step (1), the preferred gradual heating range is 50-150° C. with a reaction time up to 3-15 minutes.

In the Step (2), the preferred temperature for decomposition and saponification is 140-220° C. with a time up to 2-15 minutes.

In the Step (5), the temperature of D,L-methionine potassium solution is reduced to 0-40° C. before using an organic solvent equivalent to 0.5-2 times the weight of D,L-methionine potassium solution for reversed and continuous extraction.

In the Step (5), the preferred organic solvents for reversed and continuous extraction include one or more of toluene, ethylbenzene, dimethylbenzene, n-butyl alcohol, isobutanol, n-pentanol, 2-methyl-1-butanol, isoamylol, sec-amyl alcohol, 3-pentanol, tert-amyl alcohol, n-hexyl alcohol, 4-Methyl-2-pentanol, 2-ethyl alcohol, 2-methyl amyl alcohol, heptanol, 2-heptanol, 3-heptanol, 2-ethylhexyl alcohol, 2-octanol, octanol, 3,5,5-trimethylhexanol, ether, MTBE (methyl tertiary-butyl ether), isopropyl ether, n-propyl ether, n-butyl ether, isoamyl ether, hexyl ether, 2-methyl tetrahydrofuran, anisole, ethoxybenzene, 3-methylanisole, EBE (ethyl benzyl ether), ethylene glycol diethyl ether, diethylene dipropyl ether and ethylene glycol di-butyl ether.

Some oil soluble viscous by-products might be produced during preparation of 5-(β-methylthioethyl)glycolyurea and D,L-methionine potassium. These by-products can be extracted by the aforesaid organic solvents; whereas D,L-methionine is a highly water soluble substance, which is unlikely dissolved in the aforesaid organic solvents. Therefore, by-products are eliminated in time through extraction by organic solvents.

In the Step (6), the temperature for continuous crystallization is 0-40° C.; whereas reaction fluid is to stay inside the continuous crystallizer for 0.5-5 hours.

In the Step (9), temperature and pressure of decomposition column are 110-160° C. and 0.15-0.8 MPa with decomposition reaction time up to 1-4 hours.

The reaction formula in the Step (1) is:

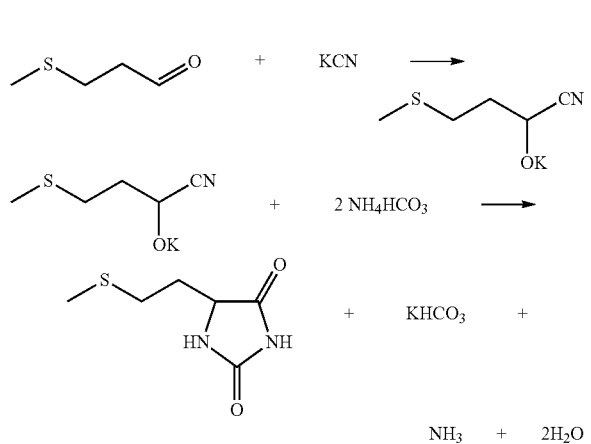

The reaction formula in the Stem (2) and (3) are.

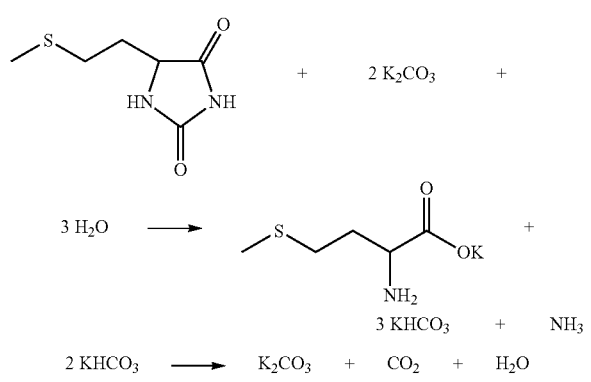

The reaction formula in the Step (4) is:

The reaction formula in the Step (6) is:

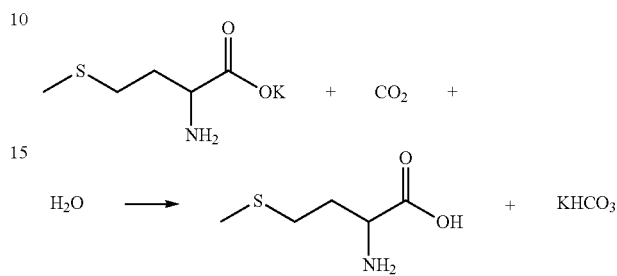

The reaction formula in the Step (9) is:

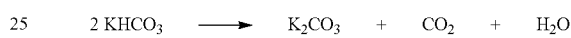

The reaction formula in the Step (10) is:

In the Step (5), by-products produced during reaction are eliminated by means of extraction so as to ensure repeated and unlimited recycling of process water.

The present invention aims to decompose $KHCO_3$ into $K_2CO_3$ through heating, and use $K_2CO_3$-containing crystallization mother solution as HCN absorption liquid to prepare KCN solution. This eliminates the need to add other metal salt during the whole technical process so as to lay down a solid foundation for recycling of process water in the whole preparation process.

To ensure a clean process, $NH_3$ and $CO_2$ gases produced during preparation of 5-(β-methylthioethyl)glycolyurea of the present invention and saponification are to subject to absorption to form $NH_4HCO_3$ again; whereas $NH_4HCO_3$ is a material as required for the preparation of 5-(β-methylthioethyl)glycolyurea. This aims to ensure maximum utilization of auxiliary materials as produced during the technical process.

According to analysis of industrialized production process, D,L-methionine preparation process using methods as reported in existing literatures may produce a large quantity of wastewater. Furthermore, N and S-containing organic compounds in the wastewater may result in serious environmental pollution and high process cost. The process of the present invention can prevent production of wastewater from the source. Furthermore, comprehensive utilization of exhaust gas produced during production can basically prevent production of exhaust gas during technical process. On this account, D,L-methionine synthesis technique of the present invention is a clean technical approach in accommodation with industrialized production.

BRIEF DESCRIPTION OF DRAWINGS

FIG. 1 is the flow chart for the present invention.

In the drawing, T1 is a HCN absorption column; T2 is a $CO_2$ and $NH_3$ absorption column; R1 is the first tubular reactor; R2 is a pressure relief tank; R3 is the second tubular reactor; T3 is a desorption column; T4 is a continuous extraction column; T5 is an organic solvent recycling and distillation column; T6 is a continuous crystallizer; S1 is the first solid-liquid separator; R4 is a scrubber; S2 is the second solid-liquid separator; T7 is a $KHCO_3$ decomposition column.

DETAILED DESCRIPTION OF THE INVENTION

The present invention is described in reference to the following specific embodiments. These embodiments are only for explanation, which shall not be deemed as restriction of scope or implementation method of the present invention.

Embodiment 1

A metering liquid delivery pump was used to deliver treated crystallization mother solution (10% $K_2CO_3$ solution was used at the initial start-up) to the HCN absorption column T1 at the flow rate of 700 Kg/h. Meanwhile, 5.4 Kg/h HCN gas was delivered to the HCN absorption column for preparation of a KCN solution in the HCN absorption column T1, and a liquid delivery pump was used to deliver the KCN solution to the first tubular reactor R1. A liquid delivery pump was used to deliver ammonium bicarbonate absorbing ammonia gas and carbon dioxide in the $CO_2NH_3$ absorption column T2 to the first tubular reactor R1 (16% ammonia bicarbonate solution was used at the initial start-up) at the velocity of 200 Kg/h, and a liquid delivery pump was used to deliver 3-methylthio propionaldehyde to the first tubular reactor R1 at the velocity of 20.8 Kg/h simultaneously. The reaction fluid was stayed for 7 minutes respectively at the temperature of 50° C. and 100° C., and stayed for another 1 minute at the temperature of 150° C. The reaction fluid discharged from the first tubular reactor R1 was subject to decompression in the decompression tank R2 to discharge surplus ammonia gas and carbon dioxide to $CO_2$ and $NH_3$ absorption column T2 to obtain 910 Kg/h 5-(β-methylthioethyl)glycolyurea solution.

A liquid delivery pump was used to deliver the prepare 5-(β-methylthioethyl)glycolyurea solution to the second tubular reactor R3 at the velocity of 910 Kg/h. The reaction fluid was stay in the second tubular reactor for 15 minutes at the temperature of 140° C. for saponification prior to decompression in the T3 absorption column. A ammonia gas and carbon dioxide produced during reaction were discharged to the $CO_2$ and $NH_3$ absorption column T2 for absorption. The saponification liquid was cooled down to the temperature of 40° C. in the heat exchanger, which was further delivered to the continuous extraction column via the pump at the velocity of 906 Kg/h. Meanwhile, 453 Kg/h ethylene glycol dipropyl ether was delivered to the continuous extraction column T4 for continuous reversed extraction. Continuous differential distillation of ethylene glycol dipropyl ether layer was conducted in the organic solvent recycling distillation column T5 to recycle the solvent for circulated use during extraction process, and incinerate tailings at the same time. A water layer was delivered to the continuous crystallizer T6 at the velocity of 935 Kg/h, and simultaneously $CO_2$ gas was delivered to the continuous crystallizer T6 for acidification until PH value of the reaction system is up to 8. Continuous crystallization was conducted at the temperature of 40° C., and the reaction fluid stayed in continuous crystallizer for 3 hours. The crystallization liquid was subject to continuous centrifugal solid-liquid separation in the first solid-liquid separator S1 to filtrate crude D,L-methionine product, and prepare a crystallization mother solution for further use. A solid delivery equipment was used to deliver crude D,L-methionine product to the scrubber R4 for spiral agitation and washing in the specified quantity at the velocity of 34 Kg/h. Meanwhile, 40 Kg/h water was continuously delivered to the scrubber R4 to control temperature of materials in the scrubber R4 below 5° C. The solid material was stayed in the scrubber R4 for 15 minutes. The intermixture subjected to continuous agitation and washing in the scrubber R4 was under continuous centrifugal solid-liquid separation via the second solid-liquid separator S2. The washing filtrate was poured into the crystallization mother solution, and D,L-methionine as filtered was airflow dried at the temperature of 110° C. under the protection of $N_2$ to obtain finished 27.5 Kg/h D,L-methionine product. Inspection was conducted according to GB-T17810-2009 Feed Grade DL-Methionine to obtain the result that methionine content was up to 99.5%, and total molar reaction yield based on 3-methylthio propionaldehyde was up to 92.3%.

The crystallization mother solution and washing filtrate were delivered to $KHCO_3$ decomposition column T7 at the velocity of 977 Kg/h, and they stayed for 1 hour at the temperature of 160° C. to totally decompose potassium hydrogen carbonate as contained in the mother solution into potassium carbonate. Meanwhile, 210 Kg/h water and 45 Kg/h ethylene diglycol ether were prepared through distillation at the column top. The distilled water was circulated to the scrubber R4 for agitation prior to further use at 40 Kg/h, whereas remaining 170 Kg/h distilled water was used in the $CO_2$ and $NH_3$ absorption column T2. Distilled ethylene diglycol ether was circulated to the extraction column T4 for further use, whereas $CO_2$ gas discharged through decomposition was used for acidification and crystallization in continuous crystallizer T6 after compression. Potassium carbonate solution containing mother solution discharged from the column bottom was cooled prior to circulation to HCN absorption column T1 for absorption of formonitrile.

Embodiment 2

A metering liquid delivery pump was used to deliver treated crystallization mother solution (10% $K_2CO_3$ solution was used at the initial start-up) to the T1 HCN absorption column at the flow rate of 552 Kg/h. Meanwhile, HCN gas was delivered to the HCN absorption column at 5.94 Kg/h for preparation of the KCN solution in the HCN absorption column T1, and a liquid delivery pump was used to deliver the KCN solution to the first tubular reactor R1. A liquid delivery pump was used to deliver ammonium bicarbonate absorbing ammonia gas and carbon dioxide in the $CO_2NH_3$ absorption column T2 to the first tubular reactor R1 (16% ammonia bicarbonate solution was used at the initial start-up) at the velocity of 250 Kg/h, and a liquid delivery pump was used to deliver 3-methylthio propionaldehyde to the first tubular reactor R1 at the velocity of 20.8 Kg/h simultaneously. The reaction fluid stayed for 3 minutes respectively at the temperature of 60° C. and 120° C., and stayed for another 1 minute at the temperature of 150° C. The reaction fluid discharged from the first tubular reactor R1 was subject to decompression in the decompression tank R2 to discharge surplus ammonia gas and carbon dioxide to $CO_2$ and $NH_3$ absorption column T2 to obtain 805 Kg/h 5-(β-methylthioethyl)glycolyurea solution. A liquid delivery pump was used to deliver 5-(β-methylthioethyl)glycolyurea solution prepared to the second tubular reactor R3 at the velocity of 805 Kg/h. The reaction fluid stayed in the second tubular reactor for 2 minutes at the temperature of 220° C. for saponification prior to decompression in the T3 absorption column. Ammonia gas and carbon dioxide produced during reaction were discharged to $CO_2$ and $NH_3$ absorption column T2 for absorption. The saponification liquid was cooled down to the temperature of 0° C. in the heat exchanger, which was further delivered to continuous extraction column T4 via the pump at the velocity of 800 Kg/h. Meanwhile, 1600 Kg/h ethylene glycol dipropyl ether was delivered to the continuous extraction column T4 for continuous reversed extraction. Continuous differential distillation of ethylene glycol dipropyl ether layer was conducted in the organic solvent recycling distillation column T5 to recycle the solvent for circulated use during extraction process, and incinerate tailings at the same time. A water layer was delivered to the continuous crystallizer T6 at the velocity of 790 Kg/h, and simultaneously $CO_2$ gas was delivered to continuous crystallizer T6 for acidification until PH value of the reaction system was up to 6. Continuous crystallization was conducted at the temperature of 0° C., and the reaction fluid stayed in the continuous crystallizer for 0.5 hour. The crystallization liquid was subject to continuous centrifugal solid-liquid separation in the first solid-liquid separator S1 to filtrate crude D,L-methionine product, and the crystallization mother solution was prepared for further use. A solid delivery equipment was used to deliver crude D,L-methionine product to the scrubber R4 for spiral agitation and washed in the specified quantity at the velocity of 34 Kg/h. Meanwhile, 102 Kg/h water was continuously delivered to the scrubber R4 and the temperature of materials in the scrubber R4 was controlled below 0° C. The solid material stayed in the scrubber R4 for 5 minutes. Continuous centrifugal solid-liquid separation of intermixture was conducted subjecting to continuous agitation and washing in the scrubber R4 via the second solid-liquid separator S2. Washing filtrate was poured into the crystallization mother solution, and the filter cake of D,L-methionine filtered at the temperature of 110° C. was airflow dried under the protection of $N_2$ to obtain 27.2 Kg/h finished D,L-methionine product. Inspection was conducted according to GB-T17810-2009 Feed Grade DL-Methionine to obtain the results that methionine content was up to 99.3%, and total molar reaction yield as based on 3-methylthio propionaldehyde was up to 91.3%.

Crystallization mother solution and washing filtrate were delivered to the $KHCO_3$ decomposition column T7 at the velocity of 890 Kg/h, and they stayed for 3 hours at the temperature of 130° C. to decompose potassium hydrogen carbonate as contained in the mother solution into potassium carbonate. Meanwhile, 312 Kg/h water and 5 Kg/h toluene were obtained through distillation at the column top. 102 Kg/h distilled water was circulated to the scrubber R4 for agitation prior to further use; whereas remaining 210 Kg/h distilled water was used in the $CO_2$ and $NH_3$ absorption column T2. Distilled toluene was circulated to the extraction column T4 for further use; whereas $CO_2$ gas discharged through decomposition was used for acidification and crystallization in continuous crystallizer T6 after compression. Potassium carbonate solution containing mother solution discharged from the column bottom was cooled prior to circulation to HCN absorption column T1 for absorption of formonitrile.

Embodiment 3

A metering liquid delivery pump was used to deliver treated crystallization mother solution (10% $K_2CO_3$ solution was used at the initial start-up) to the HCN absorption column T1 at the flow rate of 828 Kg/h. Meanwhile, 5.67 Kg/h HCN gas was delivered to the HCN absorption column for preparation of the KCN solution in the HCN absorption column T1, and a liquid delivery pump was used to deliver the KCN solution to the first tubular reactor R1. A liquid delivery pump was used to deliver ammonium bicarbonate absorbing ammonia gas and carbon dioxide in $CO_2NH_3$ absorption column T2 to the first tubular reactor R1 (16% ammonia bicarbonate solution was used at the initial start-up) at the velocity of 300 Kg/h, and a liquid delivery pump was used to deliver 3-methylthio propionaldehyde to the first tubular reactor R1 at the velocity of 20.8 Kg/h simultaneously. The reaction fluid stayed for 1 minutes and 2 minutes respectively at the temperature of 90° C. and 120° C., and stayed for another 2 minutes at the temperature of 150° C. The reaction fluid discharged from the first tubular reactor R1 was subject to decompression in the decompression tank R2 to discharge surplus ammonia gas and carbon dioxide to T2 $CO_2$ and $NH_3$ absorption column T2 to obtain 1122 Kg/h 5-(β-methylthioethyl)glycolyurea solution.

A liquid delivery pump was used to deliver the prepared 5-(β-methylthioethyl)glycolyurea solution to the second tubular reactor R3 at the velocity of 1122 Kg/h. The reaction fluid stayed in the second tubular reactor R3 for 4 minutes at the temperature of 200° C. for saponification prior to decompression in the T3 absorption column. The produced ammonia gas and carbon dioxide during reaction were discharged to $CO_2$ and $NH_3$ absorption column T2 for absorption. The saponification liquid was cooled down to the temperature of 20° C. in the heat exchanger, which was further delivered to the continuous extraction column T4 via the pump at the velocity of 1117 Kg/h. Meanwhile, 1000 Kg/h ethylene glycol dipropyl ether was delivered to the continuous extraction column T4 for continuous reversed extraction. Continuous differential distillation of ethylene glycol dipropyl ether layer in the organic solvent recycling distillation column T5 was conducted to recycle the solvent for circulated use during extraction process, and incinerate tailings at the same time. A water layer was delivered to continuous crystallizer T6 at the velocity of 1130 Kg/h, and simultaneously $CO_2$ gas was delivered to the continuous crystallizer T6 for acidification until PH value of the reaction system is up to 8. Continuous crystallization was conducted at the temperature of 20° C., and the reaction fluid stayed in continuous crystallizer for 5 hours. The crystallization liquid was subject to continuous centrifugal solid-liquid separation in the first solid-liquid separator to filtrate crude D,L-methionine product, and crystallization mother solution was prepared for further use. A solid delivery equipment was used to deliver crude D,L-methionine product to the scrubber R4 for spiral agitation and washing in the specified quantity at the velocity of 35 Kg/h. Meanwhile, 70 Kg/h water was continuously delivered to the scrubber R4 to control temperature of materials in the scrubber R4 below 20° C.; solid material is to be stay in the scrubber R4 for 10 minutes; proceed with continuous centrifugal solid-liquid separation of intermixture subjecting to continuous agitation and washing in the scrubber R4 via the second solid-liquid separator S2; pour washing filtrate into the crystallization mother solution, and proceed with airflow drying of filter cake of D,L-methionine as filtered at the temperature of 140° C. under the protection of $N_2$ to obtain 27.9 Kg/h finished D,L-methionine product. Proceed with inspection as per GB-T17810-2009: Feed Grade DL-methionine to make sure that methionine content is up to 99.4%, and total molar reaction yield as based on 3-methylthio propionaldehyde is up to 93.6%.

Deliver crystallization mother solution and washing filtrate to $KHCO_3$ decomposition column T7 at the velocity of 1207 Kg/h, and let them to stay for 4 hours at the temperature of 110° C. to decompose potassium hydrogen carbonate as contained in the mother solution into potassium carbonate. Meanwhile, 328 Kg/h water and 25 Kg/h amyl carbinol were prepared through distillation at the column top. 70 Kg/h distilled water was circulated to the scrubber R4 for agitation prior to further use; whereas remaining 258 Kg/h distilled water was used to $CO_2$ and $NH_3$ absorption column T2. Distilled amyl carbinol was circulated to the extraction column T4 for further use; whereas $CO_2$ gas discharged through decomposition was used for acidification and crystallization in the continuous crystallizer T6 after compression. Potassium carbonate solution contained mother solution as discharged from the column bottom was cooled prior to circulation to the HCN absorption column T1 for absorption of formonitrile.

Embodiment 4

A metering liquid delivery pump was used to deliver treated crystallization mother solution (10% $K_2CO_3$ solution was used at the initial start-up) to the HCN absorption column T1 at the flow rate of 700 Kg/h. Meanwhile, 5.4 Kg/h HCN gas was delivered to the HCN absorption column for preparation of the KCN solution in HCN absorption column T1, and a liquid delivery pump was used to deliver the KCN solution to the first tubular reactor R1. A liquid delivery pump was used to deliver ammonium bicarbonate absorbing ammonia gas and carbon dioxide in the $CO_2NH_3$ absorption column T2 to the first tubular reactor R1 (16% ammonia bicarbonate solution was used at the initial start-up) at the velocity of 200 Kg/h, and a liquid delivery pump was used to deliver 3-methylthio propionaldehyde to the first tubular reactor R1 at the velocity of 20.8 Kg/h simultaneously. The reaction fluid stayed for reaction for 3 minutes at the temperature of 150° C. The reaction fluid discharged from the first tubular reactor R1 was subject to decompression in the decompression tank R2 to discharge surplus ammonia gas and carbon dioxide to the $CO_2$ and $NH_3$ absorption column T2 to obtain 910 Kg/h 5-(β-methylthioethyl)glycolyurea solution.

A liquid delivery pump was used to deliver the prepared 5-(β-methylthioethyl)glycolyurea solution to the second tubular reactor R3 at the velocity of 910 Kg/h. The reaction fluid stayed in the second tubular reactor R3 for 10 minutes at the temperature of 170° C. for saponification prior to decompression in the T3 absorption column. The produced ammonia gas and carbon dioxide during reaction were discharged to the $CO_2$ and $NH_3$ absorption column T2 for absorption. The saponification liquid was cooled down to the temperature of 10° C. in the heat exchanger, which was further delivered to continuous extraction column T4 via the pump at the velocity of 905 Kg/h. Meanwhile, 905 Kg/h ethylene glycol dipropyl ether was delivered to the continuous extraction column T4 for continuous reversed extraction. Continuous differential distillation of the ethylene glycol dipropyl ether layer in the organic solvent recycling distillation column T5 was conducted to recycle the solvent for circulated use during extraction process, and incinerate tailings at the same time. A water layer was delivered to the continuous crystallizer T6 at the velocity of 915 Kg/h, and simultaneously $CO_2$ gas was delivered to the continuous crystallizer T6 for acidification until PH value of the reaction system was up to 7.5. Continuous crystallization was conducted at the temperature of 10° C., and the reaction fluid stayed in the continuous crystallizer for 2 hours. The crystallization liquid was subject to continuous centrifugal solid-liquid separation in the first solid-liquid separator S1 to filtrate crude D,L-methionine product, and the crystallization mother solution was prepared for further use. A solid delivery equipment was used to deliver crude D,L-methionine product to the scrubber R4 for spiral agitation and washing in the specified quantity at the velocity of 35 Kg/h. Meanwhile, 35 Kg/h water was continuously delivered to the scrubber R4 to control temperature of materials in the scrubber R4 below 10° C. The solid material stayed in the scrubber R4 for 10 minutes. The intermixture subjected to continuous agitation and washing in the scrubber R4 was under continuous centrifugal solid-liquid separation via the second solid-liquid separator S2. The washing filtrate was poured into the crystallization mother solution, and the filter cake of D,L-methionine as filtered was airflow dried at the temperature of 130° C. under the protection of $N_2$ to obtain 28.0 Kg/h finished D, L-methionine product. Inspection was conducted according to GB-T17810-2009 Feed Grade DL-methionine to obtain the results that methionine content was up to 99.2%, and total molar reaction yield as based on 3-methylthio propionaldehyde was up to 94.0%.

The crystallization mother solution and washing filtrate were delivered to the $KHCO_3$ decomposition column T7 at the velocity of 947 Kg/h, and they stayed for 1.5 hours at the temperature of 150° C. to decompose potassium hydrogen carbonate as contained in the mother solution into potassium carbonate. Meanwhile, 207 Kg/h water and 18 Kg/h diethyl ether were prepared through distillation at the column top. The distilled water was circulated to the scrubber R4 at 35 Kg/h for agitation prior to further use; whereas remaining 172 Kg/h distilled water was used to the $CO_2$ and $NH_3$ absorption column T2. The distilled diethyl ether was circulated to the extraction column T4 for further use; whereas $CO_2$ gas discharged through decomposition was used for acidification and crystallization in continuous crystallizer T6 after compression. The potassium carbonate solution containing mother solution discharged from the column bottom was cooled prior to circulation to HCN absorption column T1 for absorption of formonitrile.

Embodiment 5

A metering liquid delivery pump was used to deliver treated crystallization mother solution (10% $K_2CO_3$ solution was used at the initial start-up) to the HCN absorption column T1 at the flow rate of 838 Kg/h. Meanwhile, 5.5 Kg/h HCN gas was delivered to the HCN absorption column for preparation of the KCN solution in the HCN absorption column T1, and a liquid delivery pump was used to deliver the KCN solution to the first tubular reactor R1. A liquid delivery pump was used to deliver ammonium bicarbonate absorbing ammonia gas and carbon dioxide in the $CO_2NH_3$ absorption column T2 to the first tubular reactor R1 (16% ammonia bicarbonate solution was used at the initial start-up) at the velocity of 220 Kg/h, and a liquid delivery pump was used to deliver 3-methylthio propionaldehyde to the first tubular reactor R1 at the velocity of 20.8 Kg/h simultaneously. A reaction fluid stayed for 3 minutes respectively at the temperature of 60° C. and 100° C., and stayed for another 4 minutes at the temperature of 140° C. The as discharged reaction fluid from the first tubular reactor R1 was subject to decompression in the decompression tank R2 to discharge surplus ammonia gas and carbon dioxide to the $CO_2$ and $NH_3$ absorption column T2 to obtain 1062 Kg/h 5-(β-methylthioethyl)glycolyurea solution.

A liquid delivery pump was used to deliver the prepared 5-(β-methylthioethyl)glycolyurea solution to the second tubular reactor R3 at the velocity of 1062 Kg/h. A reaction fluid stayed in the second tubular reactor for 9 minutes at the temperature of 190° C. for saponification prior to decompression in the T3 absorption column. Ammonia gas and carbon dioxide produced during reaction were discharged to the $CO_2$ and $NH_3$ absorption column T2 for absorption. The saponification liquid was cooled down to the temperature of 30° C. in the heat exchanger, which was further delivered to the continuous extraction column T4 via the pump at the velocity of 1056 Kg/h. Meanwhile, 1200 Kg/h ethylene glycol dipropyl ether was delivered to the continuous extraction column T4 for continuous reversed extraction. Continuous differential distillation of the ethylene glycol dipropyl ether layer was conducted in the organic solvent recycling distillation column T5 to recycle the solvent for circulated use during extraction process, and incinerate tailings at the same time. A water layer was delivered to continuous crystallizer T6 at the velocity of 1050 Kg/h, and simultaneously $CO_2$ gas was delivered to continuous crystallizer T6 for acidification until PH value of the reaction system was up to 9. Continuous crystallization was conducted at the temperature of 30° C., and the reaction fluid stayed in continuous crystallizer for 3 hours. The crystallization liquid was subject to continuous centrifugal solid-liquid separation in the first solid-liquid separator S1 to filtrate crude D,L-methionine product, and the crystallization mother solution was prepared for further use. A solid delivery equipment was used to deliver crude D, L-methionine product to the scrubber R4 for spiral agitation and washing in the specified quantity at the velocity of 35 Kg/h. Meanwhile, 60 Kg/h water was continuously delivered to the scrubber R4 to control temperature of materials in the scrubber R4 below 30° C. The solid material stayed in the scrubber R4 for 10 minutes. The intermixture subjected to continuous agitation and washing in the scrubber R4 was under continuous centrifugal solid-liquid separation via the second solid-liquid separator S2. A washing filtrate was poured into the crystallization mother solution, and the filter cake of D,L-methionine as filtered was airflow dried at the temperature of 130° C. under the protection of $N_2$ to obtain 27.8 Kg/h finished D, L-methionine product. Inspection according to GB-T17810-2009 Feed Grade DL-Methionine was conducted to obtain the result that methionine content was up to 99.3%, and total molar reaction yield as based on 3-methylthio propionaldehyde was up to 93.3%.

The crystallization mother solution and washing filtrate were delivered to the $KHCO_3$ decomposition column T7 at the velocity of 1106 Kg/h, and they stayed for 3 hours at the temperature of 120° C. to decompose potassium hydrogen carbonate contained in the mother solution into potassium carbonate. Meanwhile, 245 Kg/h water and 7 Kg/h 2-ethyl-hexyl alcohol were prepared through distillation at the column top. The distilled water was circulated to the scrubber R4 at 60 Kg/h for agitation prior to further use; whereas remaining 185 Kg/h distilled water was used in the $CO_2$ and $NH_3$ absorption column T2. Distilled 2-ethylhexyl alcohol was circulated to the extraction column T4 for further use; whereas $CO_2$ gas discharged through decomposition was used for acidification and crystallization in continuous crystallizer T6 after compression. The potassium carbonate solution containing mother solution discharged from the column bottom was cooled prior to circulation to the HCN absorption column T1 for absorption of formonitrile.

The invention claimed is:
1. A clean method for preparing D,L-methionine, comprising the following steps:
  (1) preparing a 5-(β-methylthioethyl)glycolyurea reaction fluid by using 3-methylthio propionaldehyde, KCN and $NH_4HCO_3$ solutions as raw materials for continuous reaction in the tubular reactor that is gradually heated;
  (2) decompressing the 5-(β-methylthioethyl)glycolyurea reaction fluid to separate NH3 and CO2 for delivery to another tubular reactor for decomposition and saponification to obtain a saponification reaction fluid;
  (3) eliminating $NH_3$ and $CO_2$ produced during saponification through desorption of the saponification fluid to obtain a D,L-methionine potassium solution;
  (4) obtaining a $NH_4HCO_3$ solution through water spray and absorption of $NH_3$ and $CO_2$ as separated in steps (2) and (3), and directly using use the $NH_4HCO_3$ solution as a material for preparation of the 5-(β-methylthioethyl) glycolyurea reaction fluid in step (1);
  (5) cooling down the D,L-methionine potassium solution in step (3), and then using an organic solvent for reversed and continuous extraction; directly using an organic solvent recycled through distillation of an organic solvent layer for reversed and continuous extraction; raffinate produced by distillation being treated as waste fluid;
  (6) delivering water that is produced through counter-current and continuous extraction in step (5) to a continuous crystallizer, simultaneously delivering $CO_2$ gas to the continuous crystallizer for acidification to control PH value of reaction fluid in the continuous crystallizer at 6-9, and then obtaining a crystallization intermixture;
  (7) separating solid and liquid in the crystallization intermixture to obtain crude D,L-methionine product and a crystallization mother solution; washing crude D,L-methionine product with water for solid-liquid separation to obtain a filter cake of D,L-methionine and washing filtrate;
  (8) drying the filter cake of D,L-methionine under the protection of inert gas to obtain D,L-methionine product;
  (9) combining the crystallization mother solution and the washing filtrate from step (7) for delivery to a decomposition column to fully decompose $KHCO_3$ into $K_2CO_3$ for release of $CO_2$ gas; released $CO_2$ gas that is subjected to compression is delivered to continuous crystallizer for acidification and crystallization;
  (10) using the $K_2CO_3$ containing mother solution as obtained in step (9) for absorption of HCN gas to prepare a KCN solution that is the material for preparation of 5-(β3-methylthioethyl)glycolyurea in step (1).

2. The clean method for preparing D,L-methionine according to claim 1, characterized in that, in the step (1), a mole ratio of 3-methylthio propionaldehyde, KCN and $NH_4HCO_3$ is 1:1-1.1:2-3.

3. The clean method for preparing D,L-methionine according to claim 1, characterized in that, in the step (1), a gradual heating range is 50-150° C. with reaction time up to 3-15 minutes.

4. The clean method for preparing D,L-methionine according to claim 1, characterized in that, in the step (2), the temperature for decomposition and saponification is 140-220° C. with time up to 2-15 minutes.

5. The clean method for preparing D,L-methionine according to claim 1, characterized in that, in the step (5), the temperature of the D, L-methionine potassium solution is reduced to 0-40° C. before using the organic solvent equivalent to 0.5-2 times the weight of the D, L-methionine potassium solution for reversed and continuous extraction.

6. The clean method for preparing D,L-methionine according to claim 1, characterized in that, in the step (5), the organic solvent for reversed and continuous extraction includes one or more of toluene, ethylbenzene, dimethylbenzene, n-butyl alcohol, isobutanol, n-pentanol, 2-methyl-1-butanol, isoamylol, sec.-amyl alcohol, 3-pentanol, tert-amyl alcohol, n-hexyl alcohol, 4-methyl-2-pentanol, 2-ethyl alcohol, 2-methyl amyl alcohol, heptanol, 2-heptanol, 3-heptanol, 2-ethylhexyl alcohol, 2-octanol, octanol, 3,5,5-trimethylhexanol, ether, methyl tertiary-butyl ether, isopropyl ether, n-propyl ether, n-butyl ether, isoamyl ether, hexyl ether, 2-methyl tetrahydrofuran, anisole, ethoxybenzene, 3-methylanisole, ethyl benzyl ether, ethylene glycol diethyl ether, diethylene dipropyl ether and ethylene glycol di-butyl ether.

7. The clean method for preparing D,L-methionine according to claim 1, characterized in that, in the step (6), the temperature for continuous crystallization is 0-40° C., whereas the reaction fluid stays inside the continuous crystallizer for 0.5-5 hours.

8. The clean method for preparing D,L-methionine according to claim 1, characterized in that, in the step (9), the temperature and pressure of decomposition column are 110-160° C. and 0.15-0.8 MPa with decomposition reaction time up to 1-4 hours.

9. The clean method for preparing D,L-methionine according to claim 5, characterized in that, in the step (5), the organic solvent for reversed and continuous extraction includes one or more of toluene, ethylbenzene, dimethylbenzene, n-butyl alcohol, isobutanol, n-pentanol, 2-methyl-1-butanol, isoamylol, sec.-amyl alcohol, 3-pentanol, tert-amyl alcohol, n-hexyl alcohol, 4-methyl-2-pentanol, 2-ethyl alcohol, 2-methyl amyl alcohol, heptanol, 2-heptanol, 3-heptanol, 2-ethylhexyl alcohol, 2-octanol, octanol, 3,5,5-trimethylhexanol, ether, methyl tertiary-butyl ether, isopropyl ether, n-propyl ether, n-butyl ether, isoamyl ether, hexyl ether, 2-methyl tetrahydrofuran, anisole, ethoxybenzene, 3-methylanisole, ethyl benzyl ether, ethylene glycol diethyl ether, diethylene dipropyl ether and ethylene glycol di-butyl ether.

\* \* \* \* \*